(12) United States Patent
Newman et al.

(10) Patent No.: US 7,693,566 B2
(45) Date of Patent: Apr. 6, 2010

(54) METHOD AND APPARATUS FOR BUFFERING ELECTROPHYSIOLOGICAL SIGNALS DURING AN MRI PROCEDURE

(75) Inventors: Richard Newman, Victoria (AU); Warwick Edward Freeman, Victoria (AU)

(73) Assignee: Compumedics Limited, Abbotsford (AU)

( * ) Notice: Subject to any disclaimer, the term of this patent is extended or adjusted under 35 U.S.C. 154(b) by 1372 days.

(21) Appl. No.: 10/967,400

(22) Filed: Oct. 18, 2004

(65) Prior Publication Data
US 2006/0084849 A1   Apr. 20, 2006

(51) Int. Cl.
*A61B 5/05* (2006.01)
*A61B 5/04* (2006.01)
*G01V 3/00* (2006.01)

(52) U.S. Cl. .................. 600/411; 600/544; 324/309
(58) Field of Classification Search .............. 600/301, 600/410, 544; 128/653; 324/309, 318, 322
See application file for complete search history.

(56) References Cited

U.S. PATENT DOCUMENTS

| 3,911,899 | A | * | 10/1975 | Hattes | .................. 600/407 |
|---|---|---|---|---|---|
| 4,248,244 | A | * | 2/1981 | Charnitski et al. | .......... 600/519 |
| 5,239,265 | A |  | 8/1993 | Sugahara |  |
| 5,436,564 | A |  | 7/1995 | Kreger et al. |  |
| 5,445,162 | A |  | 8/1995 | Ives |  |
| 5,485,220 | A | * | 1/1996 | McNeilly et al. | ............. 348/525 |
| 5,500,188 | A | * | 3/1996 | Hafeman et al. | ....... 204/403.01 |
| 6,397,099 | B1 | * | 5/2002 | Chance | ........................ 600/473 |
| 6,751,499 | B2 | * | 6/2004 | Lange et al. | ................. 600/544 |
| 7,076,283 | B2 | * | 7/2006 | Cho et al. | .................... 600/410 |
| 2003/0088161 | A1 | * | 5/2003 | Stengel et al. | .............. 600/301 |

FOREIGN PATENT DOCUMENTS

EP    1 273 922 A1    1/2003

\* cited by examiner

*Primary Examiner*—Eric F Winakur
*Assistant Examiner*—Michael T Rozanski
(74) *Attorney, Agent, or Firm*—Sughrue Mion, PLLC

(57) ABSTRACT

The subject invention overcomes the problem of electrical interference in signals taken during an MRI procedure by using a long cable and a unity gain buffer amplifier near the patient, with a low output impedance to drive the cable and thus greatly reduce the capacitively coupled interference. Passive low pass filtering is incorporated prior to the buffer amplifier to attenuate high frequency interference from the MRI system. Since the buffer amplifier requires no digital signals and does not emit high frequency signals, it does not interfere with the MRI system.

17 Claims, 2 Drawing Sheets

METHOD AND APPARATUS FOR BUFFERING ELECTROPHYSIOLOGICAL SIGNALS DURING AN MRI PROCEDURE

BACKGROUND OF THE INVENTION

Magnetic Resonance Imaging (MRI) is a medical technique for creating cross-sectional images of the body which are then used to diagnose injury or disease. A typical MRI system will use powerful radio waves and cylindrical magnets to manipulate the natural magnetic properties of the human body. Essentially, an MRI system monitors resonant movements of hydrogen atoms as they are alternately magnetized and bombarded with radio waves. The state of hydrogen in diseased or injured tissue is different than in normal tissue and so they are more readily detected under a typical MRI procedure.

When patients are undergoing an MRI procedure to obtain information about their internal tissue structure, it is sometimes beneficial to simultaneously obtain electrophysiological data, to further aid in the patient's diagnosis or to monitor the patient's condition. For example, it may be beneficial to utilize electroencephalograms (EEG) or electrocardiograms (ECG) in conjunction with an MRI system. However, obtaining electrophysiological data via prior art devices may create electromagnetic interference that corrupts the MRI procedure. Alternatively, the MRI device may create electromagnetic interference which corrupts electrophysiological data transmitted via prior art approaches.

For example, modern EEG machines normally use high speed digital switching signals to acquire the EEG waveforms in a digital format suitable for viewing and processing by a computer. This requires an analog to digital converter (ADC) to transform the EEG into a binary representation, typically 8 to 24 bits, of the original analog signal. This binary signal is then readily transferred to a computer through a standard interface such as the USB, Parallel port or Ethernet port. Digital signals have very fast switching edges which can generate interfering harmonics in the tens of megahertz frequency range even though the fundamental digital signal frequency may be only a few kilohertz. A major problem is that these high frequency harmonics can radiate from equipment located near the MRI machine and interfere with the imaging process. Consequently, major sources of high frequency emissions such as computers and conventional electrophysiological records must be located outside the MRI room.

In the prior art, if the patient's EEG or ECG is to be recorded the electrode signals are sent via a long cable to the EEG machine located outside the MRI room. However, using the long cable for EEG signals allows electrical interference from the MRI system or nearby power mains to be capacitively coupled to the electrophysiological signal. The amplitude of such interference may severely degrade the EEG signal. A typical EEG signal is only 10 to 100 microvolts peak to peak and is therefore easily contaminated by main power cables which have voltages in the order of 250 to 550 volts peak to peak.

Consequently, there is a need for a method and apparatus which minimizes the amount of electromagnetic interference generated during an MRI procedure wherein a patient is concurrently being monitored.

SUMMARY OF THE INVENTION

The subject invention relates to the use of buffer amplifiers on patient electrophysiological signals taken during an MRI scan. The subject method and apparatus reduces the amount of MRI and power mains induced electromagnetic interference in the electrophysiological signal, while minimizing the amount of electromagnetic interference to the MRI system.

In one embodiment, the subject invention overcomes the problem of electrical interference in long electrophysiological cables by using a unity gain buffer amplifier near the patient, with a low output impedance to drive the cable and thus greatly reduce the capacitively coupled interference. Passive low pass filtering may be incorporated prior to the buffer amplifier to attenuate high frequency interference from the MRI system. The buffer amplifier requires no digital signals and does not emit high frequency signals so it does not interfere with the MRI system.

Electrical interference to electrophysiological signal recordings on patients undergoing MRI can be reduced by utilizing a unity gain buffer amplifier located close to the patient. The low output impedance of the buffer amplifier allows long cable runs with significantly reduced capacitively coupled interference from the MRI machine or nearby mains power wiring. The cable may be run outside the MRI room where it is connected to conventional electrophysiological recording equipment.

Furthermore, because the subject invention enables the analog to digital conversion of an electrophysiological signal to occur outside the MRI room, the subject invention reduces the amount of electromagnetic interference to the MRI system. The interference is reduced because the high frequencies generated by the digital signals involved in the analogue to digital conversion process are outside the MRI room.

BRIEF DESCRIPTION OF THE DRAWINGS AND FIGURES

For purposes of facilitating and understanding the subject matter sought to be protected, there is illustrated in the accompanying drawings an embodiment thereof. From an inspection of the drawings, when considered in connection with the following description, the subject matter sought to be protected, its construction and operation, and many of its advantages should be readily understood and appreciated.

DESCRIPTION OF THE INVENTION

Figure 1:
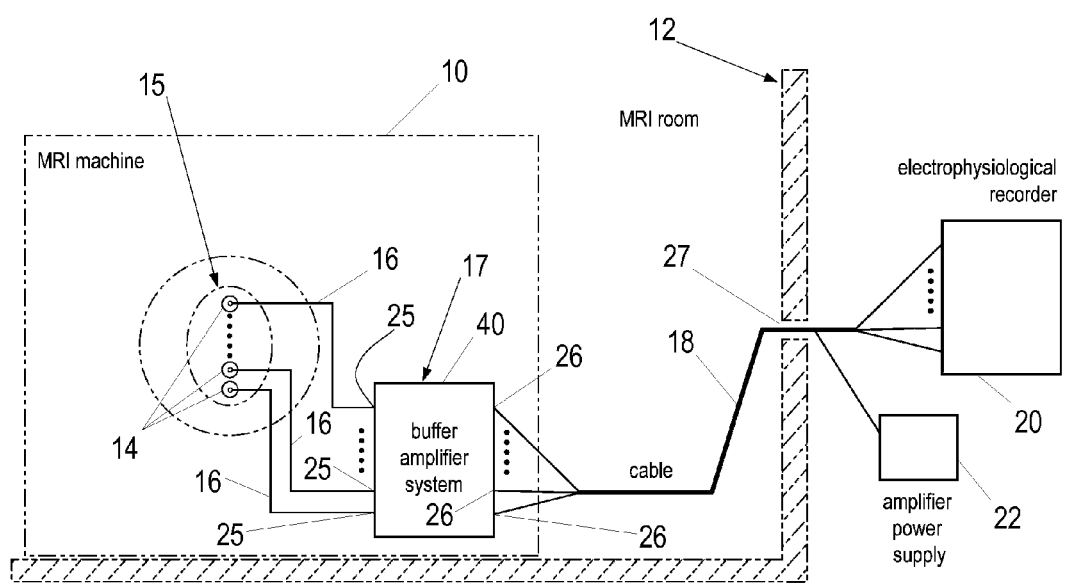
FIG. 1 is a block diagram of one embodiment of the subject invention.
Figure 2:
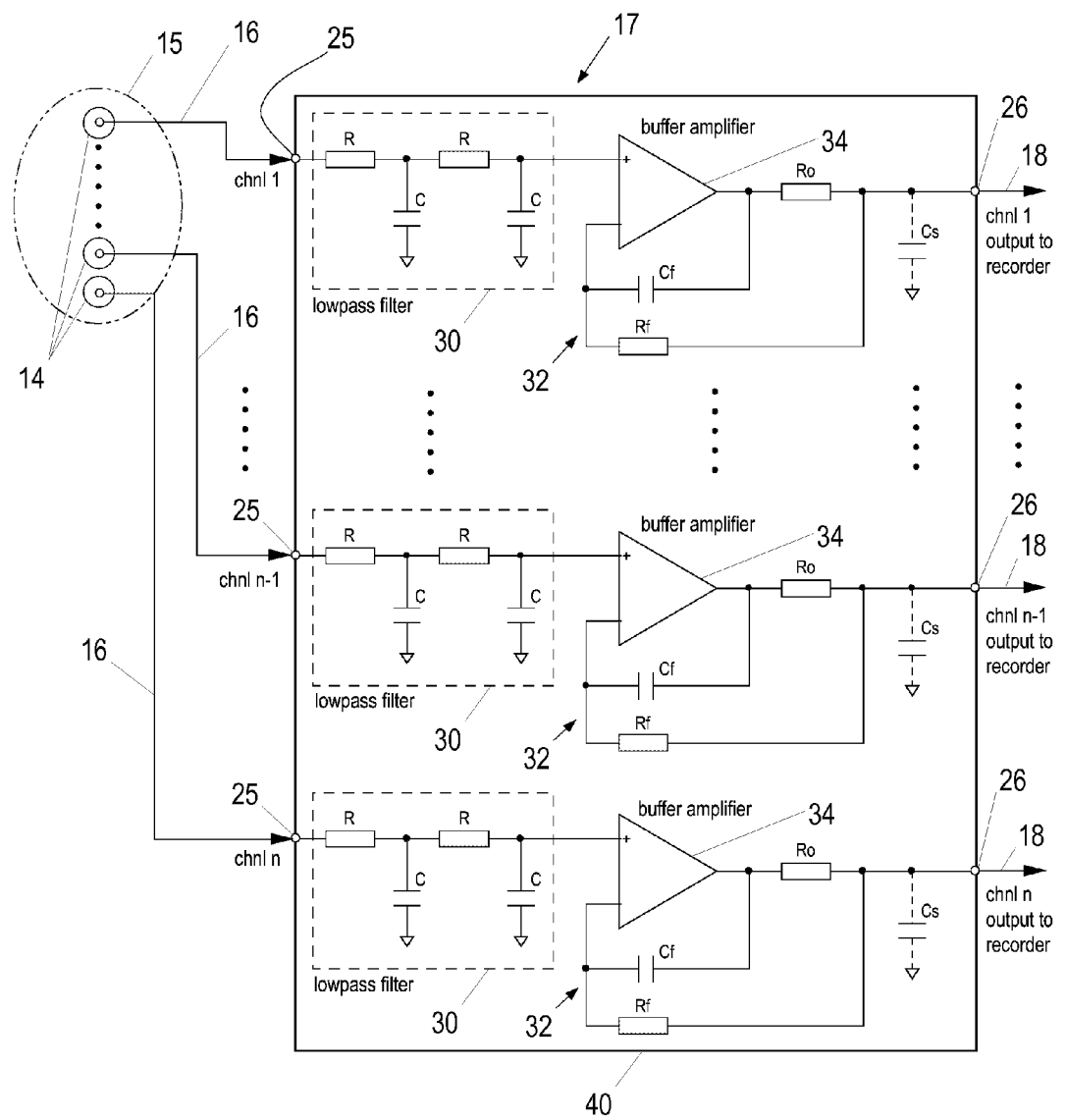
FIG. 2 is a circuit diagram of one embodiment of the buffer amplifier of FIG. 1.

As shown in FIGS. 1 and 2, the subject invention is typically utilized in an MRI procedure room which comprises an MRI system 10 and a wall or barrier system 12 which shields the MRI system 10 from electromagnetic interference. In one embodiment, the subject invention includes a plurality of sensors/electrodes 14 positioned on a patient 15 undergoing an MRI procedure. Each sensor 14 is connected via a lead wire 16 to a buffer amplifier system 17 which is located adjacent to an MRI system 10, either directly connected to the MRI system 10 or lying near the MRI system 10. A cable 18 provides a communication pathway between the buffer amplifier system 17 and an electrophysiological recorder 20 and a power supply 22 located on the opposite side of the wall 12.

In one embodiment, a patient 15 is located inside the bore of the MRI system 10 while electrodes 14 are attached thereto. Lead wires 16 transfer an electrophysiological signal from the electrodes 14 to an input port 25 of the buffer amplifier system 17. A buffered output signal is provided at output ports 26 of the buffer amplifier system 17 and is sent through cable 18 through a port 27 in the wall 12 to the electrophysiological recorder 20 located outside the MRI room. A power supply 22 located outside of the MRI room is connected in circuit to the buffer system through the cable 18 to provide power to the buffer amplifier system 17. This power supply 22 may include one or more batteries.

In one embodiment, the buffer amplifier system 17, as shown in more detail in FIG. 2, includes a plurality of low pass filters 30 and buffer amplifiers 32. The electrophysiological signals received at input ports 25 are low pass filtered using a passive RC filter 30 to reduce the amplitude of high frequency signals emanating from the MRI machine. The two pole filter shown is one of many possible low pass filters which can be used for this purpose. One skilled in the art can readily adapt known low pass filter embodiments to replace the disclosed embodiment.

In one embodiment, the buffer amplifiers 32 include operational amplifiers 34 which are unity gain stable and capable of driving large capacitive loads such as a long cable. Ideally, the operational amplifiers 34 and other components of amplifier system 17 should contain no ferromagnetic material so as not to disturb the magnetic fields in the MRI machine. The operational amplifiers 34 should also have low bias current, low noise and low distortion so as to obtain as faithful reproduction of the electrode signal as possible. Providing unity gain allows for very accurate matching between channels without using high precision resistors. An example of an operational amplifier suitable for use as operational amplifier 34 is the AD8628ART made by Analog Devices.

In one embodiment, the buffer amplifier system 17 includes a housing 40 to contain the buffer amplifiers 32 and low pass filters 30. The housing 40 can include a plurality of input ports 25 allowing each lead 16 to be coupled to an associate low pass filter 30 and buffer amplifier 32. The housing 40 can also include separate output port 26 wherein the cable 18 interfaces to each buffer amplifier 32. The buffer amplifier system 17 may be integrated to an EEG system, or any known electrophysiological monitor.

The capacitance of the cable, Cs, at the output of the buffer amplifier should be selected to prevent amplifier instability. Components Ro, Rf and Cf of the buffer amplifier 32 are chosen to stabilize the amplifier 32 in the presence of cable capacitance, Cs, by satisfying the known relationship:

$$Ro\ Cs < 0.5\ Rf\ Cf$$

The particular method of stabilizing the amplifiers 32 is unimportant.

The matter set forth in the foregoing description and accompanying drawings is offered by way of illustration only and not as a limitation. While a particular embodiment has been shown and described, it will be apparent to those skilled in the art that changes and modifications may be made without departing from the broader aspects of applicant's contribution. The actual scope of the protection sought is intended to be defined in the following claims when viewed in their proper perspective based on the prior art.

I claim:

1. A method of obtaining an electrophysiological signal from a patient undergoing an MRI procedure, the method comprising:
    detecting an electrophysiological signal from a patient undergoing an MRI procedure within an MRI procedure room;
    sending the electrophysiological signal through a buffer amplifier located inside the MRI procedure room and adjacent to an MRI system, said buffer amplifier being powered by a power supply located outside said MRI procedure room, wherein said buffer amplifier does not create electromagnetic interference during the MRI procedure; and
    receiving a buffered signal at an electrophysiological recorder located a sufficient distance from the MRI system such that the electrophysiological recorder does not create electromagnetic interference in the MRI procedure.

2. The method of claim 1, and further comprising filtering the electrophysiological signal to remove signal elements above a selected frequency.

3. The method of claim 1, and further comprising converting the electrophysiological signal into a digital signal without creating electromagnetic interference in the MRI procedure.

4. The method of claim 1, wherein the buffer amplifier has unity gain.

5. An apparatus for obtaining an electrophysiological signal during an MRI procedure comprising:
    an input port for receiving electrophysiological signals;
    a plurality of buffer amplifiers in communication with the input port, each of said plurality of buffer amplifiers being powered through a power cable from a power source located outside of an MRI procedure room, wherein said buffer amplifiers do not create electromagnetic interference during the MRI procedure;
    an output cable in communication with the buffer amplifiers, the output cable being of sufficient length to extend outside of said MRI procedure room; and
    a housing adapted to locate the input port and the buffer amplifiers inside the MRI procedure room and adjacent to an MRI system.

6. The apparatus of claim 5, wherein the buffer amplifier includes a unity gain operational amplifier.

7. The apparatus of claim 5, and further comprising a low pass filter connected in circuit between the input port and the buffer amplifier.

8. The apparatus of claim 7, wherein the low pass filter is a passive RC filter.

9. The apparatus of claim 5, and further comprising an electrophysiological recorder in communication with the output cable.

10. The apparatus of claim 9, wherein the electrophysiological recorder is an LEG machine.

11. An EEG system compatible for use with an MRI system, the system comprising:
    a plurality of EEG sensors;
    a plurality of buffer amplifiers located inside an MRI procedure room and in communication with the EEG sensors;
    a power supply in electrical connection with said plurality of buffer amplifiers, said power supply located outside of said MRI procedure room and a sufficient distance from the buffer amplifiers such that said power supply does not create electromagnetic interface interference during an MRI procedure; and
    an EEG recorder in communication with the buffer amplifiers, the EEG recorder adapted to be located a sufficient distance from an MRI system such that the EEG recorder does not create electromagnetic interference in the MRI system.

12. The LEG system of claim 11, and further comprising a low pass filter connected in circuit between the sensors and the buffer amplifiers.

13. The EEG system of claim 11, wherein the buffer amplifiers includes a unity gain operational amplifier.

14. A method of obtaining an electrophysiological signal during an MRI procedure comprising:
- locating an electrophysiological recorder a sufficient distance away from an MRI system such that the electrophysiological recorder does not interfere with the MRI procedure;
- locating a buffer amplifier system inside an MRI procedure room and adjacent to an MRI unit, said buffer amplifier system being powered by a remote power supply located outside said MRI procedure room;
- obtaining an electrophysiological signal from a patient undergoing the MRI procedure; and
- sending the electrophysiological signal to the electrophysiological recorder via the buffer amplifier.

15. The method of claim 14, and further comprising filtering the electrophysiological signal before it reaches the electrophysiological recorder.

16. The method of claim 15, wherein the filtering includes using a low pass filter on the electrophysiological signal.

17. The method of claim 14, and further comprising converting the electrophysiological signal to a digital signal at a location having a sufficient distance from the buffer amplifier such that the conversion does not create electromagnetic interference in the MRI system.

* * * * *